United States Patent [19]

Kinney et al.

[11] 3,936,472

[45] Feb. 3, 1976

[54] LACTONE ACID SYNTHESIS

[75] Inventors: Robert Earl Kinney, Lawrenceville; Albert Lloyd Williams, Hopewell Township; El-Ahmadi Ibrahim Heiba, Princeton, all of N.J.

[73] Assignee: Mobil Oil Corporation, New York, N.Y.

[22] Filed: Jan. 19, 1973

[21] Appl. No.: 324,939

[52] U.S. Cl. .................. 260/343.6; 260/326.5 FL; 260/326.5 FN; 252/54.6; 252/56 D
[51] Int. Cl.² ........................................ C07D 307/28
[58] Field of Search ...................... 260/343.6, 343.5

[56] References Cited
UNITED STATES PATENTS

| | | | |
|---|---|---|---|
| 3,155,685 | 11/1964 | Prill et al. | 260/343.6 |
| 3,155,686 | 11/1964 | Prill et al. | 260/343.6 |
| 3,755,173 | 8/1973 | Kennedy et al. | 260/343.6 |

*Primary Examiner*—Raymond V. Rush
*Assistant Examiner*—Anne Marie T. Tighe
*Attorney, Agent, or Firm*—C. A. Huggett; R. W. Barclay; S. A. Strober

[57] ABSTRACT

Alkyl lactone esters or sulfidic esters are prepared by reacting an alkenylsuccinic anhydride with an alcohol or thiol in the presence of an acid-acting catalyst. The esters are useful as dispersants or detergents in aqueous or hydrocarbon systems or they may be further reacted with amines to produce other useful additives for such systems. Esters of monohydroxy alcohols or monothiols or polyhydroxy alcohols or polythiols may be prepared and used in this invention.

14 Claims, No Drawings

LACTONE ACID SYNTHESIS

BACKGROUND OF THE INVENTION

1. Field of the Invention

This invention relates to a method of preparing lactone acid compounds in excellent yields, and more particularly this invention relates to the preparation of lactone acid esters and their use in fluid systems or as intermediates.

2. Description of the Prior Art

Copending U.S. application Ser. No. 212,626, filed on Dec. 27, 1971, now abandoned discloses the preparation of hydroxyamide soaps and lactam acetic acid amides from lactone acids. These lactone acids are the products of acid hydrolysis of alkenylsuccinic anhydrides. The preparation takes over 15 hours and achieves only about 40 to 50 percent conversion of anhydride to lactone acid, and requires a second 15-hour or more conversion or recycled unreacted anhydride. For example, a two-step 34-hour reaction cycle may yield no more than about 75% lactone acid based on initial anhydride.

U.S. Pat. Nos. 3,200,075 and 3,261,782 describe the preparation of a methyl lactone ester by reacting dimethyl bromosuccinate and an olefin in the presence of a peroxide. Cyclization to the lactone occurs through the removal of a methyl group.

SUMMARY OF THE INVENTION

Alkyl lactone esters and thioesters may be prepared directly from alkenylsuccinic anhydride at high yields by the method of reacting the anhydride with an alcohol or mercaptan in the presence of an acid-acting catalyst. The ester or thioester products of this invention may be (1) further reacted with an amine to produce lactone- or lactam-amides, (2) hydrolyzed to the lactone acid for further reaction with metal compounds or amines to produce metal or amine salts of hydroxyacids or (3) used themselves as fluid additives.

DESCRIPTION OF SPECIFIC EMBODIMENTS

One major aspect of the present invention involves the reaction between an alkenylsuccinic anhydride and an alcohol or mercaptan, also referred to herein as thiol. The reaction is an acid catalyzed esterification and lactonization. The anhydride, which may contain a single alkenyl radical or a mixture of alkenyl radicals variously bonded to the cyclic succinic anhydride group, is understood to contain a substantial proportion of

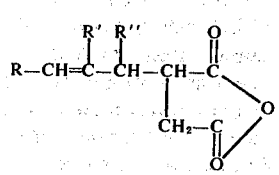

wherein R, R' and R'' may individually be hydrogen or hydrocarbyl or substituted hydrocarbyl each having from 1 to about 400 carbon atoms, and preferably from 1 to about 200 carbon atoms. This compound is obtained by well-known methods, such as the reaction between an olefin-1 and maleic anhydride or halosuccinic anhydride or succinic ester (U.S. Pat. No. 2,568,876). In branched olefins, particularly branched polyolefins, R'' may range from methyl to a longer carbon chain than R or R'. However, the exact structure may not always be ascertained and the various R groups cannot be precisely identified. In straight chain alkenyl groups, R' and R'' would be hydrogen.

Suitable olefins include butene, isobutene, pentene, decene, dodecene, tetradecene, hexadecene, octadecene, eicosene, and polymers of propylene, butene, isobutene, pentene, decene, and the like, and halogen-containing olefins. The olefins may also contain cycloalkyl and aromatic groups. It is understood that the addition of the olefin involves a shift of the unsaturated bond from the end carbon-carbon bond back to the adjacent carbon-carbon bond as shown above.

The alkenylsuccinic anhydride is reacted with an alcohol or a thiol in the presence of an acid-acting catalyst. This reaction is preferably carried out under reflux conditions for a period of from 1 to about 15 hours. The reaction is understood to open the anhydride and form a lactone ring at the unsaturated bond of the alkenyl group and an ester group, as follows:

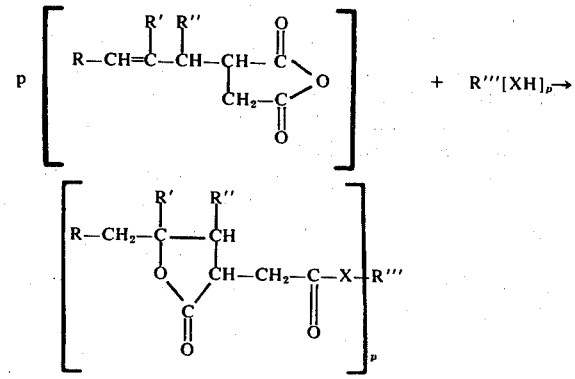

wherein R, R' and R'' are already designated, X is oxygen or sulfur, $p$ is 1 or more, and preferably 1 to 4, and R''' is hydrocarbyl, including, without limitation, alkyl, aralkyl, cycloalkyl, and the alkylene and other polyvalent forms when $p$ is greater than 1. R''' may contain from 1 to about 50, and preferably from 1 to about 30, carbon atoms and halogen and oxygen-containing derivatives thereof. R'''$[XH]_p$ may be a simple alcohol or mercaptan, such as methanol, ethanol, propanol, butanol, pentanol, neopentyl alcohol, hexanol, decanol, tetradecanol, hexadecanol, eicosanol, benzyl alcohol, cyclopentanol, cyclohexanol; methyl mercaptan, ethyl mercaptan, propyl mercaptan; halo-substituted alcohols, such as chloroethanol, iodoethanol and the like. Polyhydroxy alcohols are also suitable. These include without limimtation glycol, methyl glycol, propylene glycol, hexamethylene glycol, decamethylene glycol, cyclohexandiol isomers, 2-hydroxymethyl propanol-1, dimethylol propane, 2,2- or 2,3- dihydroxymethyl butane, 2,2,3-trihydroxymethyl butane, 2,2-dihydroxymethyl butanol-1 (also termed trimethylol propane), pentaerythritol, ether alcohols (wherein R''' contains either linkages), such as Cellosolve and methyl Cellosolve.

As the acid-acting catalyst for the reaction, any highly dissociated anhydrous acid may be used, such as phosphoric, polyphosphoric, sulfonic, arylsulfonic (p-toluene sulfonic), phosphonic and hydrogen halide. However, the heterogeneous catalysts are preferred to liquids and the cation exchange resins are most preferred since they are very effective and they permit convenient separation from the reaction mixture. Also suitable are crystalline aluminosilicates, at least partially in the hydrogen form, zeolites and synthetic aluminosilicate particularly, with such supports as alumina, vanadia, titania, chromia, chromia-alumina, zinc oxide; other oxides and sulfides, such as phosphorus pentoxide, iron sulfide, nickel sulfide and the like.

Of the preferred ion exchange resin catalyts, the strong acid resins, most preferably sulfonic acid resins, but also phenolsulfonic, phosphonic, etc., are very effective. These acid functional groups are attached to a resin matrix, such as phenolic resin, a crosslinked copolymer of styrene using any crosslinking agent, e.g. polyfunctional monomer or partial polymer, such as a styrene-divinylbenzene copolymer. Other matrices, such as acrylates, polystyrene, chlorinated styrene polymers, are also acceptable. Even sulfonated coal may be used.

Of the resulting alkyl lactone acid esters or thioesters, certain classes may be novel. Novel lactone esters are those in which R''' is alkyl, aralkyl or cycloalkyl of at least 5 carbon atoms when $p$ is 1, or R''' may be any organic radical and $p$ is 2 or greater than 2. These esters may have utility as detergents or dispersants in industrial organic fluids, such as lubricants, heat-exchange liquids, transmission fluids and the like. If the alkenyl group of the succinic anhydride reactant is straight-chain (R' and R'' are hydrogen) of about 25 carbon atoms or less, the esters may also be useful as intermediates in preparing detergents or soaps for aqueous systems. The esters derived from high molecular weight alkenylsuccinic anhydride (and R'' is methyl or higher alkyl) may be further reacted with amines to provide lactone amides or lactam amides or poly(lactam amides), or with other alcohols or thiols to provide other esters which also have detergent properties for organic fluid systems.

The most preferred alkenylsuccinic anhydrides used in this invention are those in which the alkenyl group contains a total of from 4 to 400 carbon atoms: from 4 to about 20 carbon atoms for aqueous systems; and at least 8 to 400 but preferably 10 to 300 for organic systems. The preferred alcohols or thiols from 1 to about 10 carbon atoms, i.e. methanol, ethanol or ethyl mercaptan, particularly if a metal soap or lactone or lactam amide is the desired end product; and polyhydroxy alcohols, if the ester itself is the desired end product. In preparing the amide derivatives, alkylene polyamines of the formula $H_2N(C_mH_{2m}NH)_nH$ are the preferred reactant, wherein $m$ is 2 to 4 and $n$ is from 1 to 10; especially desirable are triethylene tetramine, tetraethylene pentamine and the like. While the light molecular weight esters described in this invention evidence excellent detergent properties, the lower molecular weight esters also show unexpectedly high detergency in conjunction with metallic additives normally used in organic media. Of particular interest are the alkali and alkaline earth metal organic sulfonates, derived from alkyl, aryl, alkaryl and like sulfonates, including both neutral and "overbased" sulfonates, i.e. those having a greater metal content than stoichiometric. Techniques for increasing the metal content of sulfonates are known (usually by reacting them with carbon dioxide and metal oxides or hydroxides). Other metal salts may also be present in the organic media for a variety of functions, such as metal phosphorodithioates, carboxylates and the like.

The following examples are provided as more specific illustration of the present invention but should not be deemed to limit the scope thereof in any manner.

EXAMPLE I

Into a 5-liter flask fitted with a reflux condenser, stirrer and thermometer were added 1220 grams of a product of a reaction between polybutene of about 1300 molecular weight (about 93 carbon atoms) and maleic anhydride. About 700 grams (0.5 mole) of the added amount is the alkenylsuccinic anhydride, the remainder being unreacted polybutene. To the flask were added 1200 ml of n-octane with moderate heat (to about 50°C.) and agitation to form a solution, followed by 46 grams (1.5 mole) of methanol and 150 grams of an ion exchange resin of sulfonic acid on a vinyl-divinylbenzene copolymer matrix in bead form. The mixture was heated to reflux with stirring for 12 hours. The resulting solution was separated from the beads and filtered.

Atmospheric distillation of the solution took off 32 grams of methanol and the n-octane. The remaining 1236 grams consists of the 520 grams of polybutene and about 716 grams of the methyl ester of the corresponding lactone acetic acid. Infrared spectra show about 90% gamma-butyrolactone ester and about 10% of a delta-lactone ester.

EXAMPLE II

Into a 500-ml flask were added 100 g (0.34 mole) of n-tetradecenylsuccinic anhydride, 16.3 grams (0.51 mole) of methanol and 250 ml of n-octane. The reaction mixture was heated to reflux at about 70°C. with stirring. The temperature rose to 80°C. and was maintained at that level for two hours. Octane and excess methanol were stripped off leaving 105 grams of the half ester of n-tetradecenylsuccinic acid.

In a sealed pressure vessel, containing 47 grams of the said half ester, 15 grams of the sulfonic acid resin catalyst of Example I, 50 ml of n-octane and 10 drops of methanol, the reaction mixture was stirred and heated at 125°C. for three hours. The mixture was then cooled, diluted with ethanol and the catalyst filtered off. Ethanol and octane were evaporated leaving 41.6 grams of the methyl ester of the corresponding lactone acid.

EXAMPLE III

Into a 4-necked flask fitted with a Dean-Stark trap under a condenser, thermometer, stirrer and nitrogen inlet tube were added 1620 grams of a reaction product prepared in a manner similar to that of Example I, of which about 58 percent by weight was the methyl ester of the alkyl-gamma-butyrolactone acid (0.648 mole) and the remainder is polybutene, and 122.7 grams (0.648 mole) of tetraethylenepentamine. The reactor was swept with nitrogen and sealed under a nitrogen atmosphere. The contents of the flask were stirred and heated to 140°C. After 4 hours at this temperature, the temperature was raised to 220°C. while methanol was collected in the trap. The mixture was held at this temperature for 20 hours. The yield of resulting reaction product was 1720 grams of lactam amide.

EXAMPLE IV

Using equipment and procedure similar to that of Example III, a mixture was prepared consisting of 747 grams of a reaction product (1) prepared in a manner similar to that of Example I except that the alkyl group of the lactone acid ester contains about 64 carbon atoms, of which product about 81 percent by weight is the methyl ester of the alkyl-gamma-butyrolactone acetic acid (0.575 mole) and the remainder is polybutene, and 851 grams of a reaction product (2) prepared as in Example I except the alkyl group of the lactone acid ester contains about 190 carbon atoms, of which product about 47.5 percent by weight is the methyl ester (0.144 mole), to which mixture were added 136 grams (0.719 mole) of tetraethylenepentamine. The reaction was heated at 140°C. under nitrogen for 4 hours and at 220°C. for 20 hours with stirring. The yield of resulting reaction mixture was 1710 grams of a mixed lactam amide.

EXAMPLE V

A mixture of 16.5 grams of a lactone ester prepared by reaction of methanol with a polyisobutenyl-succinic anhydride of 1400 average molecular weight under conditions similar to that of Example I; and 12.3 grams of the polyisobutene used to prepare the anhydride was dissolved in 40 cc of n-octane in a reaction flask equipped with a reflux condenser and a Dean-Stark trap. To the flask were added 0.53 grams of trimethylolpropane and 2.0 grams of the sulfonic acid resin catalyst.

The reaction mixture was stirred and heated at reflux until infrared analysis showed that all of the hydroxyl groups of the trimethylolpropane had reacted. The resulting octane-polyester solution was washed three times with water and the octane was distilled off.

EXAMPLE VI

A mixture of 69.5 grams of the lactone ester of Example V and about 36.1 grams of polyisobutene was added to a reaction flask. To the mixture were added 2.3 grams of trimethylolpropane and 1.0 gram of p-toluene sulfonic acid. The reaction mixture was stirred and heated at 125°C. for 41 hours. An additional 0.77 gram of trimethylolpropane was added. The reaction was continued for 29 hours. Infrared analysis showed that all of the hydroxyl groups had reacted to form the polyester exchange product; also that a portion of the lactone rings had undergone a reaction to form ester linkages. The polyester was then treated as the polyester solution of Example V.

EXAMPLE VII

To the reactor similar to that of Example V were added 33 grams (0.0235 mole) of polyisobutenylsuccinic anhydride prepared from a polyisobutene of 1300 molecular weight and 17 grams of the unreacted polyisobutene and 25 ml of n-octane. The anhydride was dissolved in the octane with stirring under moderate heating. To this solution were added 3.62 grams (0.0247 mole) of 1-octanethiol (5 percent excess) and 7.5 grams of the sulfonic acid resin catalyst used in previous examples. The mixture was stirred and heated at 120°C. for 8 hours under nitrogen. Octane and the excess thiol were removed by vacuum stripping, leaving 53 grams of product (including the 17 grams of olefin). The presence of thioester was confirmed by infrared spectrum.

EXAMPLE VIII

To a reaction flask equipped with a water trap and condenser were charged 105 grams (0.075 mole) of an alkenylsuccinic anhydride of average molecular weight 1400, 12.4 grams (0.095 mole) of n-octyl alcohol, 100 ml of n-octane, and 15 grams of a sulfonic acid resin catalyst. The reaction mixture was stirred and heated at reflux for 3 hours. An additional 6.2 grams (0.047 mole) of n-octyl alcohol were added and refluxing continued for 4 hours. The reaction mixture was cooled, filtered, and the octane solvent evaporated. Infra-red analysis of the product showed complete conversion of the anhydride to the octyl ester of the corresponding lactone acid.

EXAMPLE IX

Using a procedure similar to that of Example I, 20 grams (0.068 mole) of n-tetradecenylsuccinic anhydride was dissolved in n-octane with warming and agitation, and 7.35 grams (0.072 mole or 6 percent excess) of n-hexyl alcohol were added, followed by 15 grams of sulfonic acid resin catalyst. The mixture was heated to reflux at 120° to 125°C. After 3 ½ hours, infrared spectra indicated no anhydride remaining. Heating was continued overnight; conversion was complete. The product was isolated by filtering off the catalyst and evaporating the n-octane.

EXAMPLE X

To a 250 ml flask equipped with an air-cooled Vigreux column and condenser, were charged 50 grams of lactone ester similar to that of Example II (prepared by reaction of the half methyl ester of n-tetradecenyl succinic acid with a sulfonic acid resin catalyst), and 100 cc of 6N hydrochloric acid. The reaction mixture was stirred and heat at reflux until 70 ml of distillate were collected. The residue was dissolved in chloroform, dried with anhydrous sodium sulfate, and the solvent evaporated. Infrared analysis of the product showed that the ester had been completely hydrolyzed to form the lactone acid.

In a suitable reactor, 33.5 g of the lactone acid and 9.0 g of sodium bicarbonate were heated and stirred with 80 ml of a 50/50 by weight t-butyl alcohol/H$_2$O mixture to form the corresponding sodium lactone carboxylate (by reaction with the carboxylic acid group). To the product were added 7.35 grams of ethanolamine and the mixture heated at reflux until all of the lactone was converted to the hydroxyamide

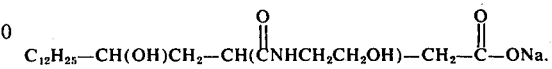

The solvent was then evaporated. A 1 percent solution of the product in distilled water was prepared. Copious suds were formed upon shaking this solution. When one volume of this solution was added to one volume of a calcium chloride solution (900 ppm hardness as calcium carbonate), no precipitate resulted and copious suds were again formed. Similar results were obtained with a magnesium sulfate solution (900 ppm hardness).

EVALUATION OF PRODUCTS

One of the characteristics of a detergent, particularly for lubricating oils, is its ability to pick up fine particulate matter, such as products of fuel combustion, from surfaces upon which they are deposited and maintain the suspension of these particles in the oil. The suspensoids can then be carried away from the operating mechanism as the oil is circulated through the system. In the following test, a lubricant composition is passed through a bed of nickel powder upon which carbon black has been deposited. The amount of carbon removed by the lubricant is measured. The greater the percent removal, the more effective is the lubricant in picking up and suspending carbon particles.

In a stainless steel cylindrical cell mounted in a constant temperature bath of 100°C., one gram of nickel powder is formed in a porous bed on a 400-mesh screen. Carbon black is deposited on the screen by passing 10 ml of a dispersion of 250 ppm of carbon black in white oil through the bed at one ml per minute followed by 5 ml of white oil alone. Then the test lubricant solution (5 ml) consisting of 5 percent by weight of a detergent additive in a refined paraffinic white oil (Nujol) is passed through at the rate of one ml per minute. The product of Example III is compared in this test with an alkenylsuccinimide prepared by reacting alkenylsuccinic anhydride, in which the alkenyl group has a formula weight of about 900, and tetraethylene pentamine. The same oil with no additive present was tested. Light transmission measurements of the test oil are made before and after the test; the percent of light transmission is proportional to the amount of carbon present (Beer-Lambert law). The following results were obtained:

| Test Oil Additive | Carbon Removed (%) |
|---|---|
| None | 0 |
| Alkenylsuccinimide | 25 |
| Example III | 54 |

Preparation of the carbon black dispersion to prepare the bed initially involves mixing 12.5 mg of 0.18 micron diameter carbon black in 50 grams of white oil and subjecting the same to ultrasonic radiation at 80 kc/sec. for 15 minutes.

Using 5 percent by weight of ester in a typical lubricating oil for passenger car lubrication as a base test medium, the esters of this invention performed in the carbon removal test with the following results:

| Test Oil Additive | Carbon Removed (%) |
|---|---|
| None | 12 |
| Example I Product | 31 |
| Example V Product | 27 |
| Example VI Product | 30. |

The oil composition used in this test (Oil A) consists of a mid-continent, solvent-refined oil of 360 SUS at 100°F., which contains an acrylate polymer additive, and 3% by weight of three metal salts, a zinc (lower alkyl) phosphorodithioate, an overbased calcium phenate and, present as one-third of the three metal salts, an overbased calcium petroleum sulfonate. The composition contains about 0.2% calcium.

The methyl ester of Example I was tested in this test in a similar base oil (Oil B) as in the previous test (except 340 SUS at 100°F.) in the presence of the above overbased calcium sulfonate (about 10% calcium) and of an overbased magnesium petroleum sulfonate (about 10% magnesium). The results are tabulated below (wherein "CaSO$_3$" and "MgSO$_3$" refer to the said overbased salts, respectively)

| Ester Conc., % | CaSO$_3$ Conc., % | Carbon Removed, % |
|---|---|---|
| 0 | 0 | 7 |
| 0 | 8 | 14 |
| 8 | 0 | 10 |
| 5 | 3 | 29 |
|  | MgSO$_3$ Conc.,% |  |
| 0 | 8 | 8 |
| 5 | 3 | 30 |

It is thus seen that the esters of this invention furnish dispersant properties to an oil formulation. Moreover, when the methyl ester is used in conjunction with a metal sulfonate, the combination displays higher dispersant characteristics than either component alone at the same total concentration.

The additives of this invention may also provide antioxidant properties to a lubricating oil or other industrial hydrocarbon fluid. The following test is used:

The test is conducted in an oxygen circulation apparatus of the type described by Dornte (Ind. Eng. Chem., 28, pages 26–30, 1936) modified so that the rate of oxygen absorption can be recorded automatically. In general, a tube containing an oil sample (30 g) and additive is placed in a heater thermostatted at 347°F. (175°C.). After thermal equilibrium is established, the sample tube is connected with a closed oxygen circulating system. Oxygen is circulated through a fritted glass disk near the bottom of the sample tube at a rate of 5 liters per hour. The smaller the amount of oxygen absorbed in a given period of time, the more stable the oil. In several examples, the time ($t_{1.0}$) required for the absorption of one mole oxygen per kilogram of oil is used to compare oils. The larger the value of $t_{1.0}$, the more stable the oil.

Sludge determinations were conducted by mixing the oxidized oil (30 grams) with 300 ml hexane, stirring overnight, and filtering through a medium frit glass filter (10 to 15 microns).

The concentration of additive in the test lubricant sample is 2 percent by weight in a solvent-refined mineral oil stock of 100 SS (at 100°F.).

The following results, using the same metal salts as in the previous carbon removal test, are:

| Additive | Sludge, mg | $t_{1.0}$, hours |
|---|---|---|
| Product of Example III | 15 | 38.2 |
| Alkenylsuccinimide | 44 | 34.0 |

Thus the method of preparing lactone acid esters as described in this invention are useful in providing intermediates for making lactone or lactam amides or metal or amine soaps. Reaction of a hydrolyzed low molecular weight lactone ester (R" is hydrogen) with alkali metal carbonates, bicarbonates or hydrides followed by reaction with an alkanolamine provides excellent hard water surfactants. The method also provides novel esters having dispersant utility alone or in combination with metal sulfonates in organic fluids. This invention, being susceptible of many derivative aspects, is not limited by any particular description herein except as defined in the following claims.

We claim:

1. A method of producing a lactone ester comprising the step of mixing alkenylsuccinic anhydride, wherein the alkenyl group has from 14 to 190 carbon atoms, with an organic compound having the formula $R'''(XH)_p$, wherein $p$ is from 1 to 4, X is selected from the group consisting of oxygen sulfur and, $R'''$ is alkyl having from 1 to 8 carbon atoms, in the presence of an acid-acting catalyst selected from the group consisting of a liquid acid selected from the group consisting of phosphoric, polyphosphoric, sulfonic, p-toluene sulfonic, phosphonic and hydrogen halide, a cation exchange resin, a crystalline aluminosilicate at least partially in the hydrogen form, and forming said lactone ester.

2. The method of claim 1 wherein X is oxygen.

3. The method of claim 1 wherein $p$ is 1.

4. The method of claim 1 wherein the organic compound is selected from the group consisting of methyl alcohol, hexyl alcohol, trimethylolpropane and octanethiol.

5. The method of claim 1 wherein the acid-acting catalyst is a sulfonic acid-ion exchange resin.

6. A compound prepared by the method of claim 1 wherein $p$ is from 2 to 4.

7. The compound of claim 6 wherein the organic compound is trimethylol propane.

8. A compound prepared by the method of claim 1 wherein $p$ is 1 and $R'''$ is alkyl having at least 5 carbon atoms.

9. The compound of claim 8 wherein the organic compound is hexyl alcohol.

10. A compound prepared by the method of claim 1 wherein the alkenyl group is polyisobutenyl.

11. The compound of claim 8 wherein the organic compound is octanethiol.

12. The compound of claim 8 wherein the organic compound is octyl alcohol.

13. The compound of claim 10 wherein the average number of carbon atoms of the polyisobutenyl is in the range of 64 to 190.

14. The method of claim 1 wherein the acid acting catalyst is p-toluene sulfonic acid.

* * * * *

UNITED STATES PATENT AND TRADEMARK OFFICE
CERTIFICATE OF CORRECTION

PATENT NO. : 3,936,472
DATED : February 3, 1976
INVENTOR(S) : ROBERT E. KINNEY, ALBERT L. WILLIAMS AND EL-AHMADI I. HEIBA It is certified that error appears in the above-identified patent and that said Letters Patent are hereby corrected as shown below:

Column 3, line 4          "either" should be --ether--

Column 3, line 64        "light" should be --high--

Signed and Sealed this

Twenty-second Day of February 1977

[SEAL]

Attest:

RUTH C. MASON
Attesting Officer

C. MARSHALL DANN
Commissioner of Patents and Trademarks